(12) United States Patent
Smith et al.

(10) Patent No.: US 7,153,649 B2
(45) Date of Patent: *Dec. 26, 2006

(54) TREATMENT OF CONGESTIVE HEART FAILURE

(75) Inventors: Eldon R. Smith, Calgary (CA); Guillermo Torre-Amione, Bellaire, TX (US)

(73) Assignee: Vasogen Ireland Limited (IE)

( * ) Notice: Subject to any disclaimer, the term of this patent is extended or adjusted under 35 U.S.C. 154(b) by 418 days.

This patent is subject to a terminal disclaimer.

(21) Appl. No.: 10/278,920

(22) Filed: Oct. 24, 2002

(65) Prior Publication Data

US 2003/0044390 A1 Mar. 6, 2003

Related U.S. Application Data

(63) Continuation of application No. 09/760,600, filed on Jan. 17, 2001, now Pat. No. 6,572,895.

(30) Foreign Application Priority Data

Jan. 18, 2000 (CA) .............................. 2296997

(51) Int. Cl.
*A01N 1/02* (2006.01)

(52) U.S. Cl. .......................................... 435/2
(58) Field of Classification Search ............... 435/2
See application file for complete search history.

(56) References Cited

U.S. PATENT DOCUMENTS

| 5,591,457 A | 1/1997 | Bolton |
| 5,834,030 A | 11/1998 | Bolton |
| 6,037,346 A | 3/2000 | Doherty, Jr. et al. |
| 6,136,308 A | 10/2000 | Tremblay et al. |
| 6,572,895 B1 * | 6/2003 | Smith et al. ................ 424/529 |

FOREIGN PATENT DOCUMENTS

| WO | WO 99/13890 | 3/1999 |
| WO | WO 00/67764 | 11/2000 |

OTHER PUBLICATIONS

Cooke, E.D., et al. "Treatment of severe Raynaud's syndrome by injection of autologous blood pretreated by heating, ozonation and exposure to ultraviolet light (H–O–U) therapy." *International Angiology*. 16(4): 250–254 (1997).

Dibbs, Z., et al. "Cytokines in Heart Failure: Pathogenetic Mechanisms and Potential Treatment." *Proceedings of the Association of American Physicians*. 111(5): 423–428 (1999).

Ganelina, I.E., et al. "Therapy of Severe Steno Cardias by UV Irradiation of the Blood and Some Action Mechanisms of this Therapy." *Folia Haematologica*. 109(3): 470–482 (1982).

Mann, D.L., et al. "Mechanisms and Models in Heart Failure: A Combinatorial Approach." *Circulation*. 100: 999–1008 (1999).

* cited by examiner

*Primary Examiner*—Michael Meller
(74) *Attorney, Agent, or Firm*—Foley & Lardner LLP

(57) ABSTRACT

A method of treating congestive heart failure (CHF) in a human patient comprises treating an aliquot of the patents blood ex vivo with at least one stressor selected from the group consisting of a temperature above or below body temperature, an electromagnetic emission and an oxidative environment, followed by administering the aliquot of treated blood to the patient. The treatment can be used on its own or as an adjunctive therapy in combination with conventional CHF treatments.

20 Claims, 7 Drawing Sheets

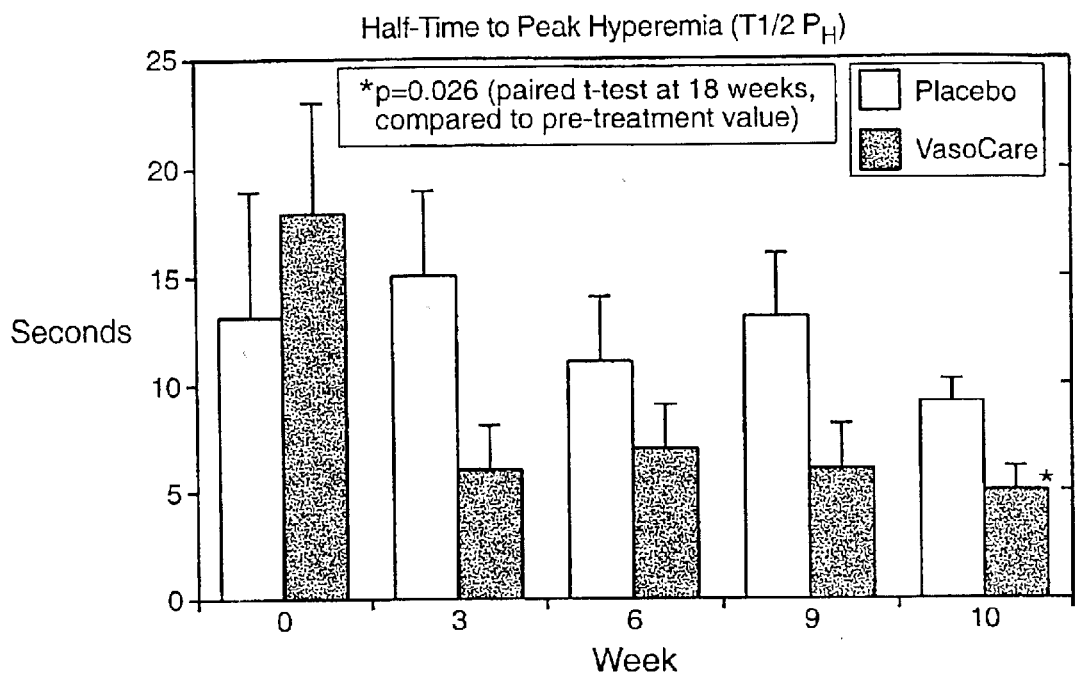
FIG._1
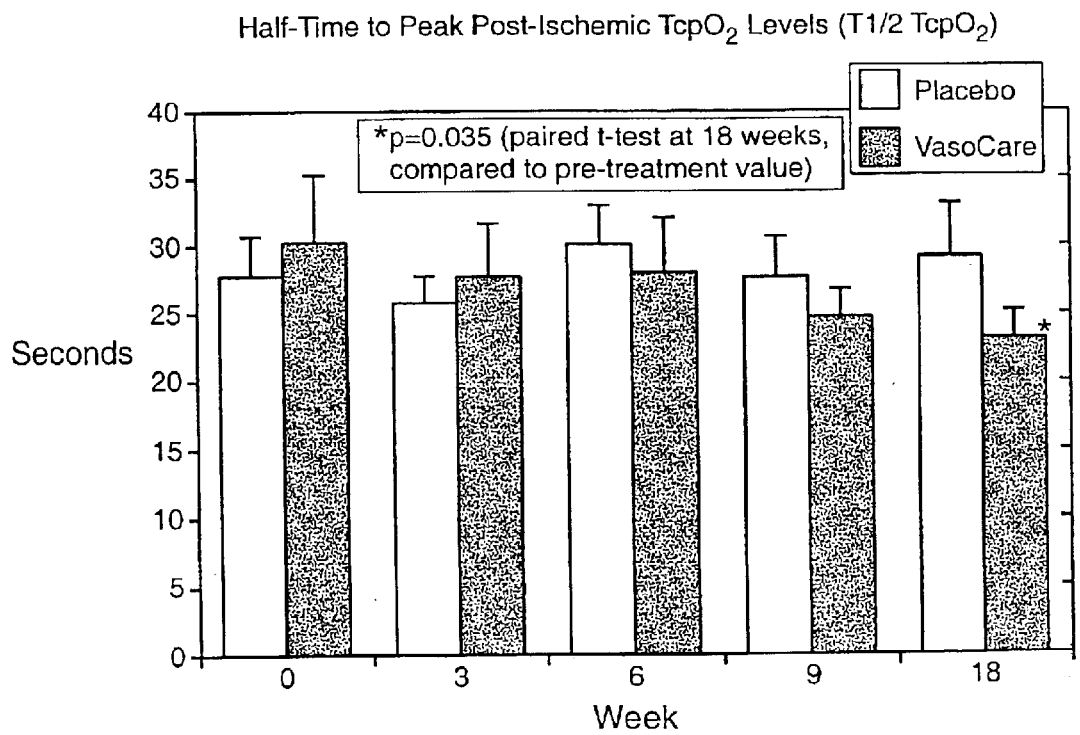
FIG._2

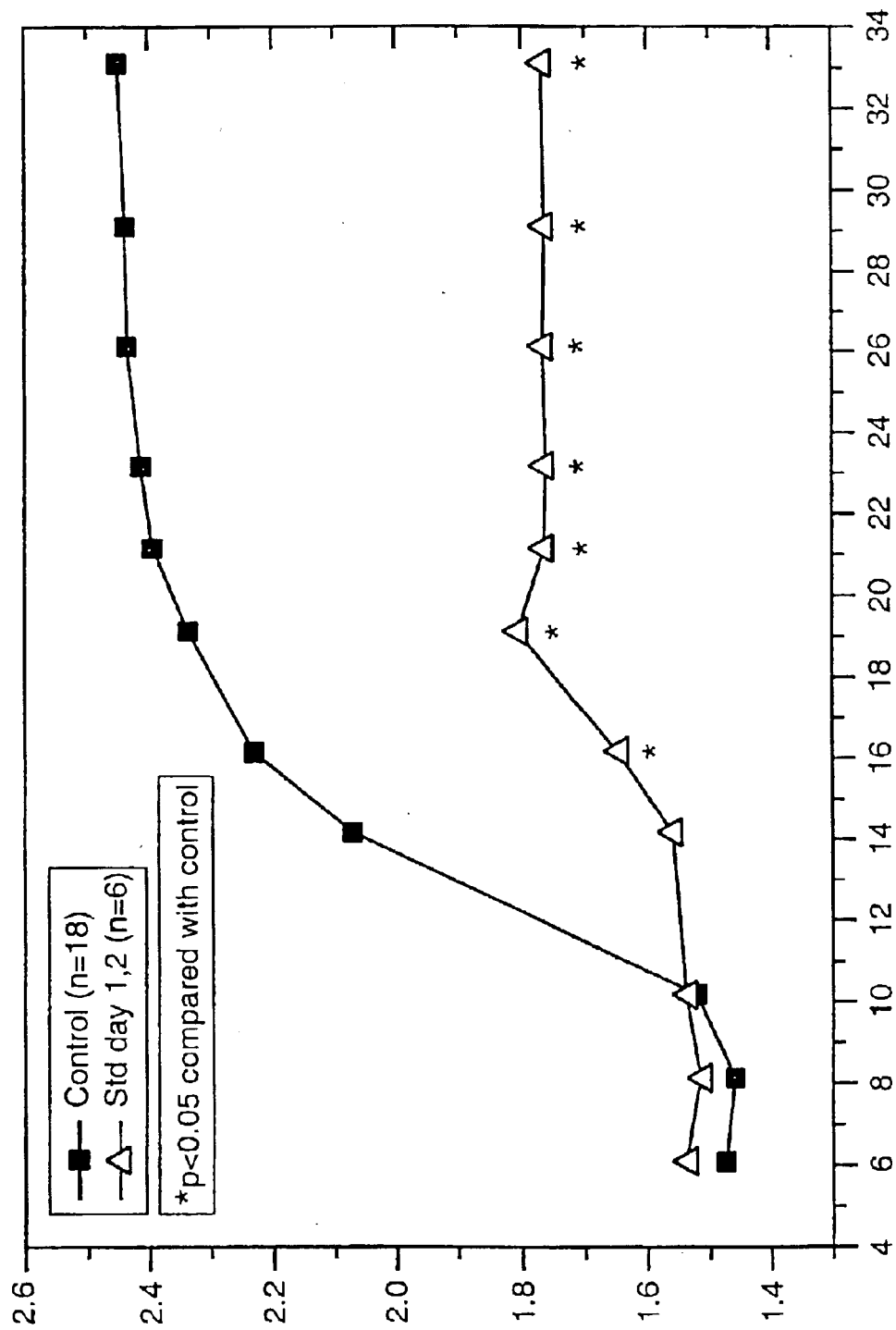
FIG._3

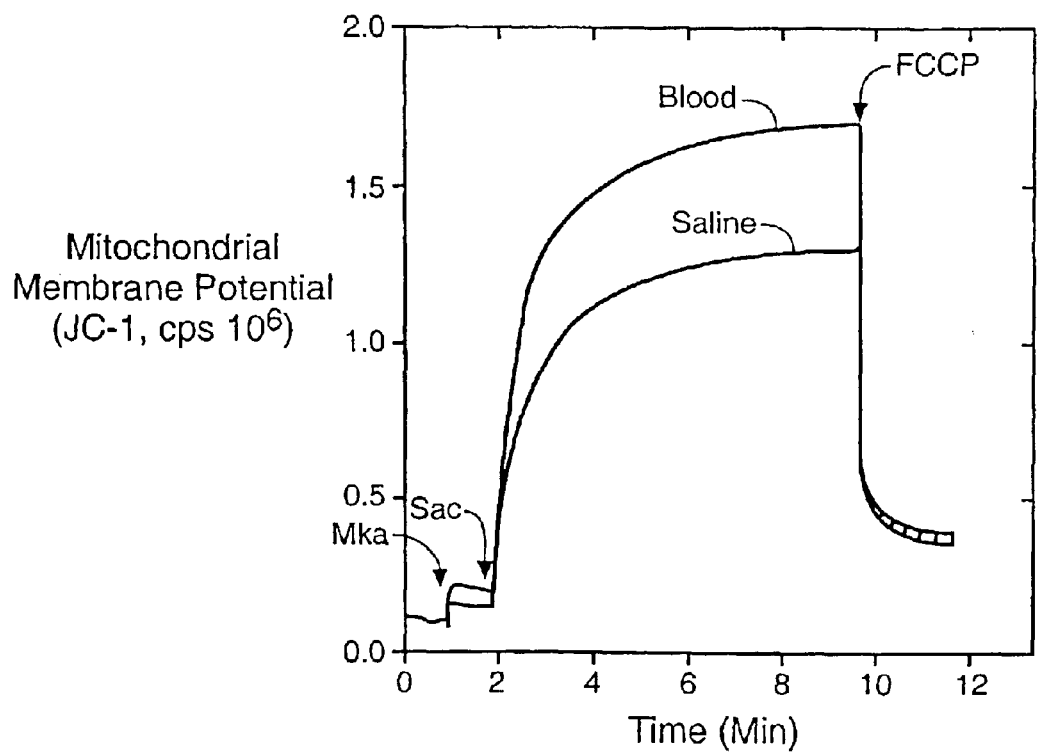
FIG._4A
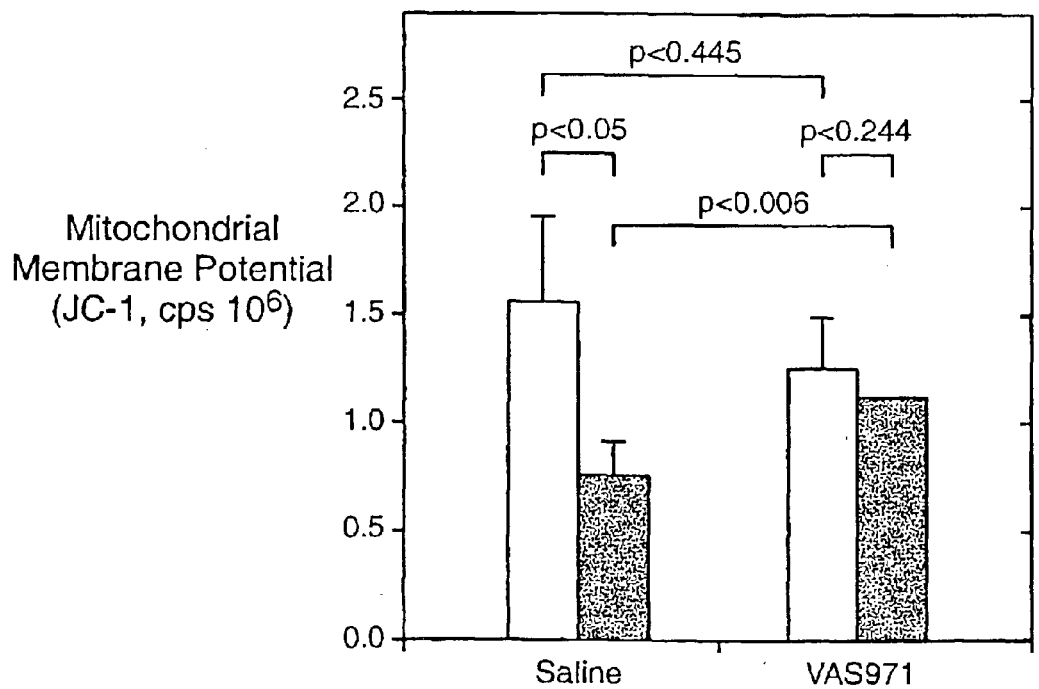
FIG._4B

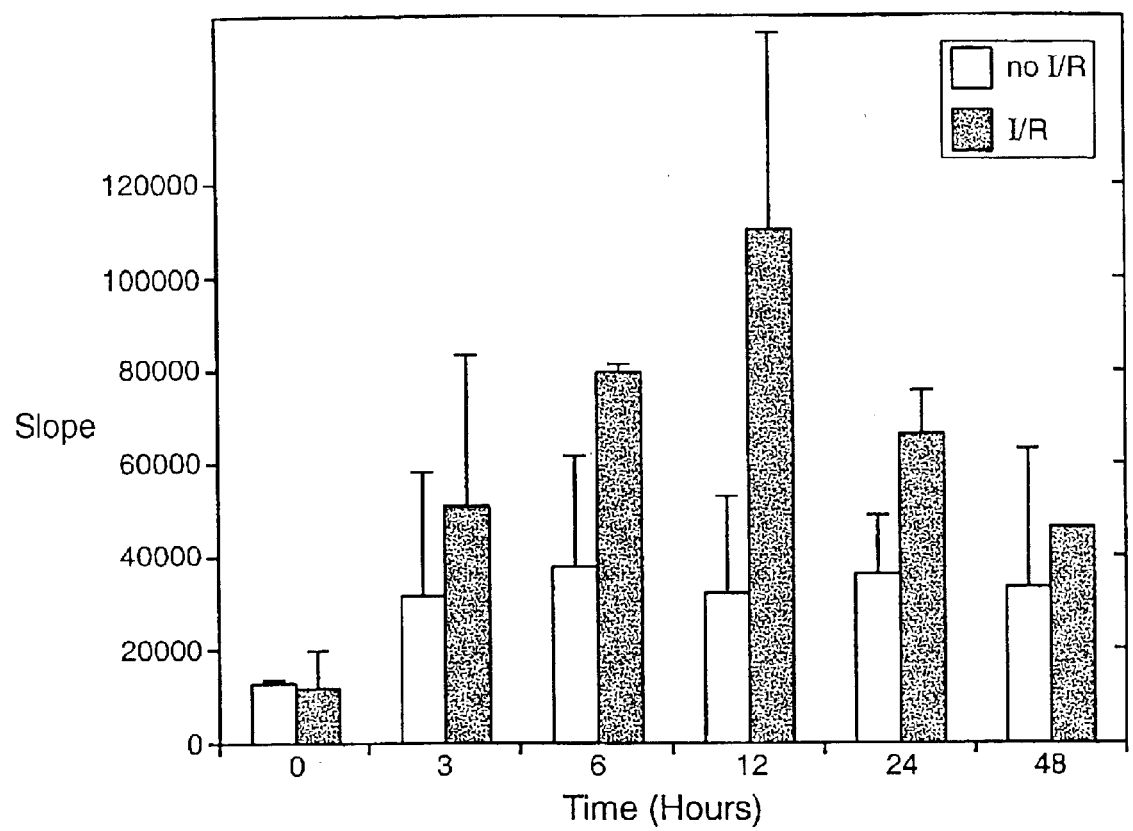
FIG._5

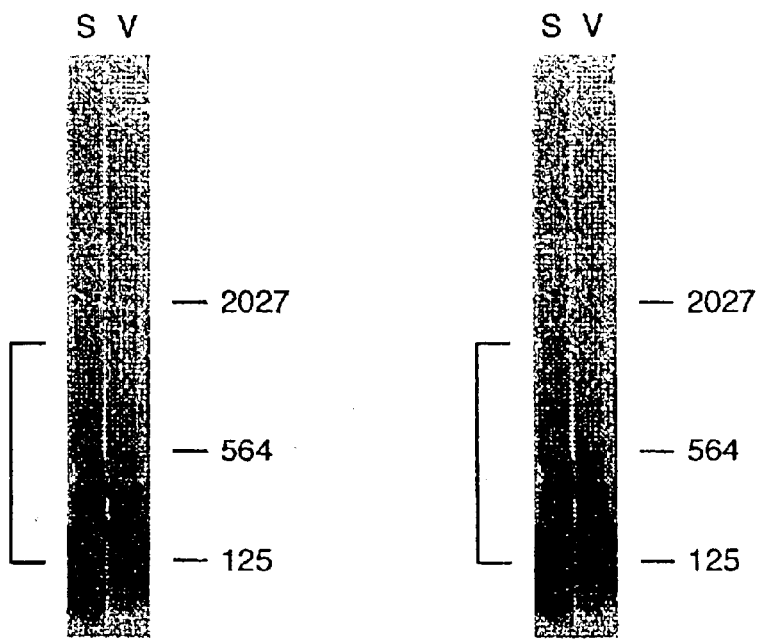
FIG._6A  FIG._7B
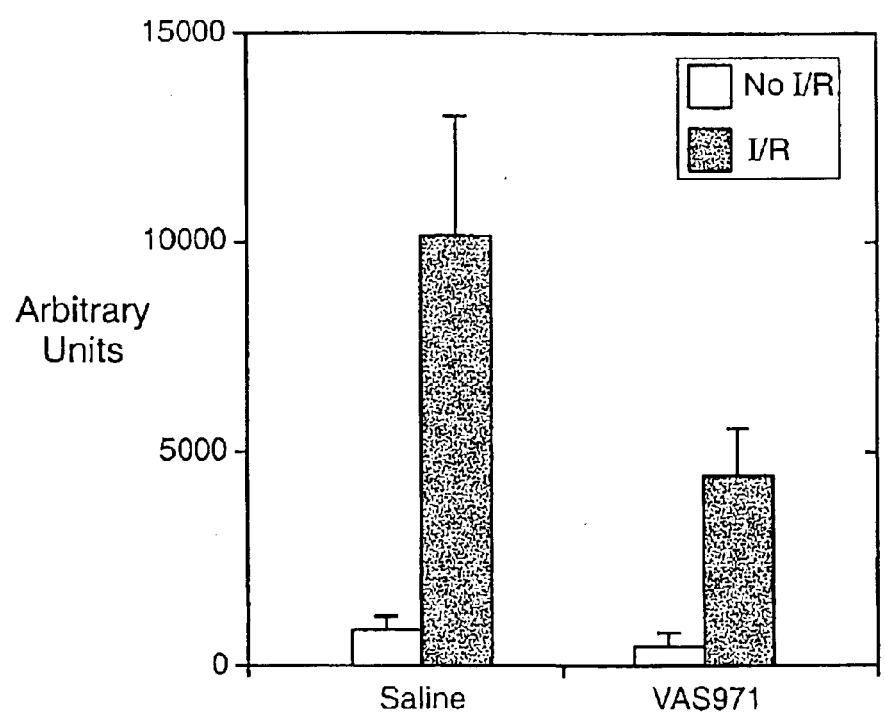
FIG._6B

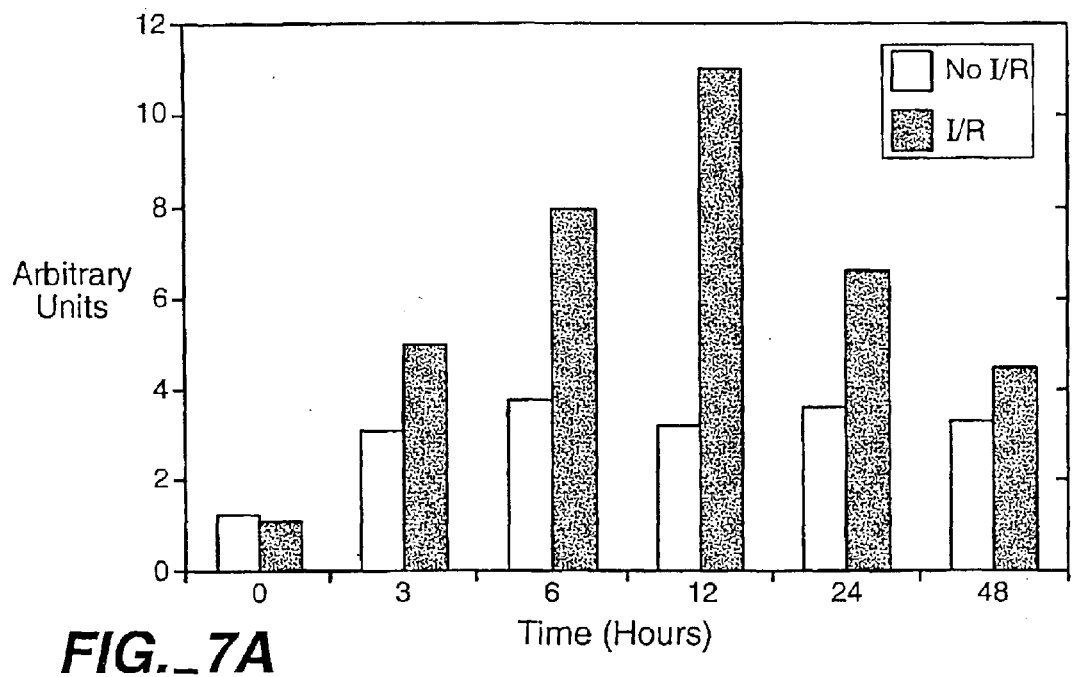
FIG._7A
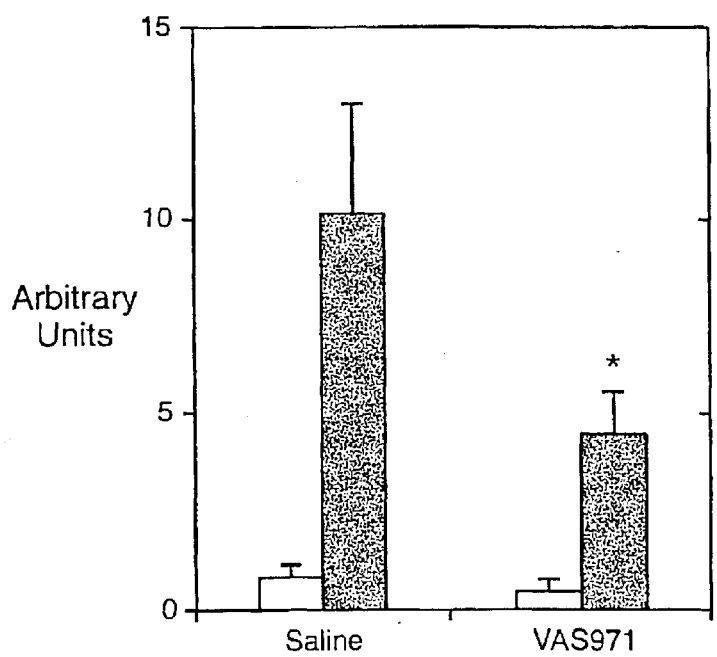
FIG._7C

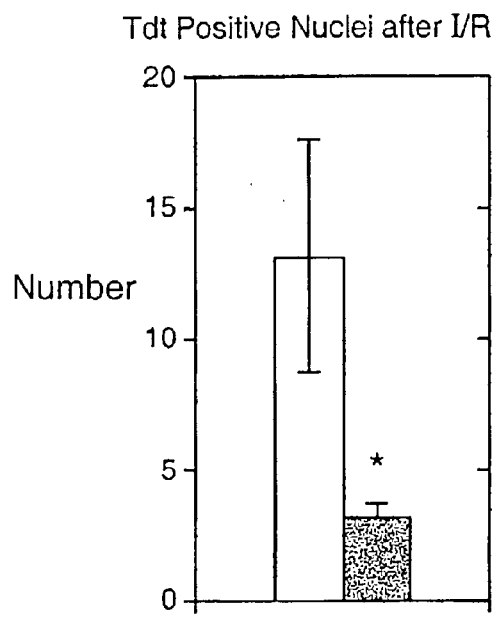
FIG._8A
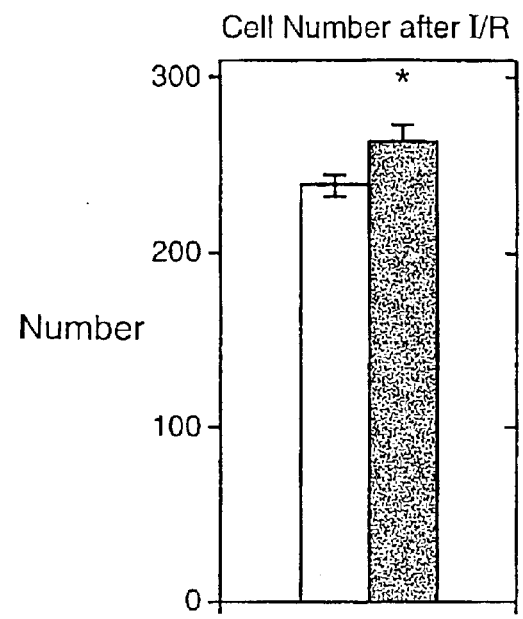
FIG._8B
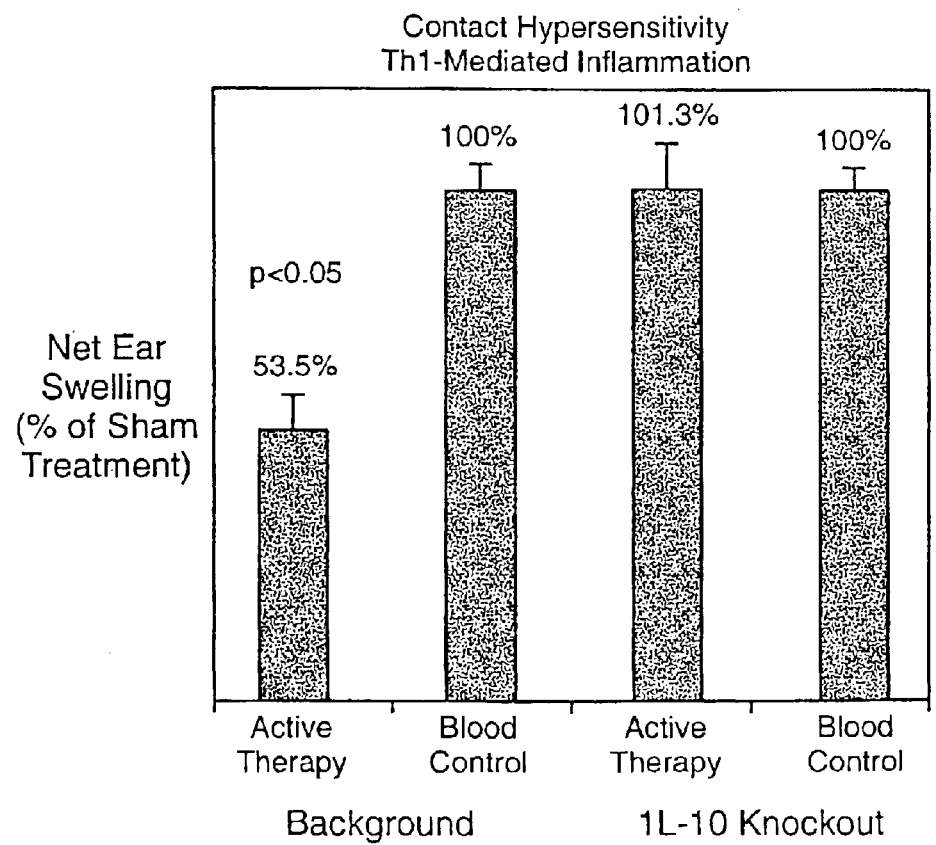
FIG._9

TREATMENT OF CONGESTIVE HEART FAILURE

This application is a continuation of Application No. 09/760,600, filed on Jan. 17, 2001, now U.S. Pat. No. 6,572,895 which issued on Jun. 3, 2003.

BACKGROUND OF THE INVENTION

1. Field of the Invention

This invention relates to methods for treating congestive heart failure, in particular by the administration to a human subject of an aliquot of modified blood, optionally in combination with one or more other treatments for alleviating the symptoms of congestive heart failure.

2. Description of the Prior Art

Congestive heart failure (CHF) is a relatively common disorder affecting approximately five million Americans, with a mortality rate of over 80,000 per year. It is believed that CHF is not a distinct disease process in itself, but rather represents the effect of multiple anatomic, functional and biologic abnormalities which interact together to ultimately produce progressive loss of the ability of the heart to fulfill its function as a circulatory pump.

CHF may be caused by the occurrence of an index event such as a myocardial infarction (heart attack) or be secondary to other causes such as hypertension or cardiac malformations such as valvular disease. The index event or other causes result in an initial decline in the pumping capacity of the heart, for example by damaging the heart muscle. This decline in pumping capacity may not be immediately noticeable, due to the activation of one or more compensatory mechanisms. However, the progression of CHF has been found to be independent of the patient's hemodynamic status. Therefore, the damaging changes caused by the disease are present and ongoing even while the patient remains asymptomatic. In fact, the compensatory mechanisms which maintain normal cardiovascular function during the early phases of CHF may actually contribute to progression of the disease, for example by exerting deleterious effects on the heart and circulation.

Some of the more important pathophysiologic changes which occur in CHF are activation of the hypothalamic-pituitary-adrenal axis, systemic endothelial dysfunction and myocardial remodeling.

Therapies specifically directed at counteracting the activation of the hypothalamic-pituitary-adrenal axis include beta-adrenergic blocking agents (β-blockers), angiotensin converting enzyme (ACE) inhibitors, certain calcium channel blockers, nitrates and endothelin-1 blocking agents. Calcium channel blockers and nitrates, while producing clinical improvement have not been clearly shown to prolong survival whereas β-blockers and ACE inhibitors have been shown to significantly prolong life, as have aldosterone antagonists. Experimental studies using endothelin-1 blocking agents have shown a beneficial effect.

Systemic endothelial dysfunction is a well-recognized feature of CHF and is clearly present by the time signs of left ventricular dysfunction are present. Endothelial dysfunction is important with respect to the intimate relationship of the myocardial microcirculation with cardiac myocytes. The evidence suggests that microvascular dysfunction contributes significantly to myocyte dysfunction and the morphological changes which lead to progressive myocardial failure.

In terms of underlying pathophysiology, evidence suggests that endothelial dysfunction may be caused by a relative lack of NO which can be attributed to an increase in vascular $O_2$ formation by an NADH-dependent oxidase and subsequent excess scavenging of NO. Potential contributing factors to increased $O_2$ production include increased sympathetic tone, norepinephrine, angiotensin II, endothelin-1 and TNF-α. In addition, levels of IL-10, a key anti-inflammatory cytokine, are inappropriately low in relation to TNF-α levels. It is now believed that elevated levels of TNF-α with associated proinflammatory cytokines including IL-6, and soluble TNF-α receptors, play a significant role in the evolution of CHF by causing decreased myocardial contractility, biventricular dilatation, and hypotension and are probably involved in endothelial activation and dysfunction. It is also believed that TNF-α may play a role in the hitherto unexplained muscular wasting which occurs in severe CHF patients. Preliminary studies in small numbers of patients with soluble TNF-receptor therapy have indicated improvements in NYHA functional classification and in patient well-being, as measured by quality of life indices.

Myocardial remodeling is a complex process which accompanies the transition from asymptomatic to symptomatic heart failure, and may be described as a series of adaptive changes within the myocardium. The main components of myocardial remodeling are alterations in myocyte biology, loss of myocytes by necrosis or apoptosis, alterations in the extracellular matrix and alterations in left ventricular chamber geometry. It is unclear whether myocardial remodeling is simply the end-organ response that occurs following years of exposure to the toxic effects of long-term neurohormonal stimulation, or whether myocardial remodeling contributes independently to the progression of heart failure. Evidence to date suggests that appropriate therapy can slow or halt progression of myocardial remodeling.

Although presently used treatments can alleviate symptoms of CHF and correct certain pathophysiologic abnormalities caused by the disease process, CHF remains a relentlessly progressive condition with a relatively high rate of mortality. In fact, relative reductions in morbidity and mortality brought about by existing drugs are on the order of about 10 to 25 percent. Therefore, the need exists for additive or superior treatments for CHF, especially those which can significantly modify the underlying disease.

SUMMARY OF THE INVENTION

The present invention overcomes at least some of the above-noted and other disadvantages of presently known CHF therapies by providing a method for treating CHF in which an aliquot of mammalian blood is treated ex vivo and subsequently introduced into the body of a mammalian subject.

The aliquot of blood is treated by being subjected to one or more stressors which have been found to modify the blood. According to the present invention, the blood aliquot can be modified by subjecting the blood, or separated cellular or non-cellular fractions of the blood, or mixtures of the separated cells and/or non-cellular fractions of the blood, to stressors selected from temperature stressors, electromagnetic emissions and oxidative environments, or any combination of such stressors, simultaneously or sequentially.

As discussed above, the pathophysiologic changes associated with CHF include immune activation, endothelial dysfunction and loss of myocytes through necrosis and/or apoptosis. The treatment method of the present invention has been shown to produce therapeutic benefits in each of these three areas.

With respect to immune activation, the treatment of the present invention has been found to modulate levels of inflammatory cytokines in several TH1/TNFα-dependent experimental inflammatory models in different species. For example, the treatment has been shown to reduce allergic contact hypersensitivity in Balb/c mice, a Th1-driven immune reaction mediated by TNF-α (Shivji et al., *Journal of Cutaneous Medicine and Surgery* 4: 132–137, 2000); to down-regulate expression of IL-6 mRNA in adjuvant-induced arthritis in the Lewis rat model of inflammatory disease; and to decrease the proportion of Th1 to Th2 cells in patients with scleroderma, a Th1-driven autoimmune disease (Rabinovich et al., Poster presented at the XII Pan-American Congress of Rheumatology, Montreal, Canada, Jun. 21–25, 1998). It is believed that the treatment down-regulates the pro-inflammatory Th1-type immune response, for example by increasing anti-inflammatory TH2-type cytokines, including IL-10.

The treatment of the Invention has been found to improve endothelial function in a number of studies conducted in humans and in animals. For example, the treatment has been found to improve endothellal-dependent vasodilator function in an open study on patients with severe primary Raynaud's disease (Cooke et al., *International Journal of Angiology* 16: 250–254, 1997), to improve the rate of recovery of skin blood flow following temporary occasion in a double-blind, placebo-controlled study in patients with advanced peripheral vascular disease secondary to atherosclerosis(Courtman et al., *Circulation* Vol 102, #18, suppl II, 2000), to reduce progression of atherosclerosis in the cholesterol-fed LDL receptor deficient mouse (Babaei et al., *Journal of the American College of Cardiology* 35 (Suppl. A): 243, 1999), and to markedly improve endothelial-dependent vasodilator function to acetylcholine in severely atherosclerotic, hypercholesteromlemic Watanabe rabbits as evidenced by an increased vasodilatory response to the nitric oxide agonist (acetyicholine) (Courtman et al., above). It is believed that the improvement in endothelial function is due to an anti-inflammatory effect and to increased availability of NO which may result in an improvement in vasodilatory capacity, known to be severely impaired in CHF patients.

With regard to myocyte loss, the method of the invention is believed to decrease levels of apoptosis and necrosis. It has been shown that the treatment can protect the kidney from ischemia/reperfusion (I/R) damage known to be associated with increased apoptotic cell death (Tremblay et al., *Pathophysiology* 5:26; Chen et al., *Medecine Sciences* 15 (Suppl. 1): 16), and can reduce apoptosis in the kidney following I/R as determined by DNA laddering and density of apoptotic nuclei stained by Tdt.

Because the treatment of the invention produces therapeutic benefits In three areas in which pathophysiologic changes occur in CHF, namely endothelial dysfunction, production of inflammatory cytokines and myocyte loss due to apoptosis, there is provided a strong theoretical basis on which to predict that the treatment of the invention would be beneficial to patients with CHF. The method of the Invention may be used as a CHF therapy on its own or In combination with other therapies, such as nitrate therapy, β-blockers, ACE inhibitors, AT receptor blocking agents, aldosterone antagonists, calcium channel blocking agents, TNF blocking agents, suppressors of production of TNF-β, and/or other more routine treatment measures such as sodium and fluid restriction, diuretics, digitalis, etc. Specific drugs known to suppress TNF-β production include pentoxifylline, amrinone, adenosine, thalidomide, TNF converting enzyme (TACE) inhibitors and dexamethasone. Specific TNF blocking agents include monoclonal antibodies and etanercept.

Accordingly, in one aspect the present invention provides a method of treating CHF in a human patient suffering therefrom, comprising: (a) treating an aliquot of the patient's blood ex vivo with at least one stressor selected from the group consisting of a temperature above or below body temperature, an electromagnetic emission and an oxidative environment; and (b) administering the aliquot of blood treated in step (a) to the patent, wherein the aliquot has a volume sufficient to alleviate CHF in the patient.

In another aspect, the present invention provides a combination treatment for CHF in a human patient suffering therefrom, the combination treatment including the administration to the patient of an aliquot of the patient's own blood which has been treated ex vivo with one or more stressors selected from an oxidative environment, thermal stress and electromagnetic emission, and a treatment selected from the group consisting of nitrates, β-blockers, ACE inhibitors, AT receptor blocking agents, aldosterone antagonists, calcium channel blocking agents, TNF blocking agents, suppressors of production of TNF-α, sodium and fluid restriction, diuretics and digitalis.

BRIEF DESCRIPTION OF THE DRAWINGS

The invention is now described, by way of example only, with reference to the accompanying drawings in which:

FIGS. 1 and 2 of the accompanying drawings are graphical presentations of the results obtained from Example 2 described below;

FIG. 3 of the accompanying drawings is a graphical presentation of the results obtained from Example 3 described below;

FIG. 4 of the accompanying drawings is a graphical presentation of the results obtained from Example 4 described below;

FIGS. 5 to 8 of the accompanying drawings are graphical presentations of the, results obtained from Example 5 described below; and FIG. 9 of the accompanying drawings is a graphical presentation of the effects of the treatment of the invention in contact hypersensitivity Th1-mediated inflammation

DETAILED DESCRIPTION OF PREFERRED EMBODIMENTS

According to a preferred process of the present invention, an aliquot of blood is extracted from a mammalian subject, preferably a human, and the aliquot of blood is treated ex vivo with certain stressors, described in more detail below. The terms "aliquot", "aliquot of blood" or similar terms used herein include whole blood, separated cellular fractions of the blood including platelets, separated non-cellular fractions of the blood including plasma. and combinations thereof. The effect of the stressors is to modify the blood, and/or the cellular or non-cellular fractions thereof, contained in the aliquot. The modified aliquot is then re-introduced into the subject's body by any route suitable for vaccination, preferably selected from intra-arterial injection. intramuscular injection, intravenous injection, subcutaneous injection, intrapertoneal injection, and oral, nasal or rectal administration.

The stressors to which the aliquot of blood is subjected ex vivo according to the method of the present invention are selected from temperature stress (blood temperature above or below body temperature), an oxidative environment and an electromagnetic emission, individually or In any combination, simultaneously or sequentially. Suitably, in human subjects, the aliquot has a volume sufficient that, when reintroduced into the subject's body, at least partial alleviation of CHF is achieved in the subject Preferably, the volume of the aliquot is up to about 400 ml, preferably from about 0.1 to about 100 ml, more preferably from about 5 to about 15 ml, even more preferably from about 8 to about 12 ml, and most preferably about 10 ml, along with an anticoagulant, e.g. 2 ml sodium citrate.

It is preferred, according to the invention, to apply all three of the aforementioned stressors simultaneously to the aliquot under treatment, in order to ensure the appropriate modification to the blood. It may also be preferred in some embodiments of the invention to apply any two of the above stressors, for example to apply temperature stress and oxidative stress, temperature stress and an electromagnetic emission, or an electromagnetic emission and oxidative stress. Care must be taken to utilize an appropriate level of the stressors to thereby effectively modify the blood to alleviate CHF in the subject.

The temperature stressor warms the aliquot being treated to a temperature above normal body temperature or cools the aliquot below normal body temperature. The temperature is selected so that the temperature stressor does not cause excessive hemolysis in the blood contained in the aliquot and so that, when the treated aliquot is injected into a subject, alleviation of CHF will be achieved. Preferably, the temperature stressor is applied so that the temperature of au or a part of the aliquot is up to about 55° C., and more preferably in the range of from about −5° C. to about 55° C.

In some preferred embodiments of the invention, the temperature of the aliquot is raised above normal body temperature, such that the mean temperature of the aliquot does not exceed a temperature of about 55° C., more preferably from about 40° C. to about 50° C., even more preferably from about 40° C. to about 44° C. and most preferably about 42.5±1° C.

In other preferred embodiments, the aliquot is cooled below normal body temperature such that the mean temperature of the aliquot is within the range of from about −5° C. to about 36.5° C., more preferably from about 10° C. to about 30° C. and even more preferably from about 15° C. to about 25° C.

The oxidative environment stressor can be the application to the aliquot of solid, liquid or gaseous oxidizing agents. Preferably, it involves exposing the aliquot to a mixture of medical grade oxygen and ozone gas, most preferably by bubbling through the aliquot, at the aforementioned temperature range, a stream of medical grade oxygen gas having ozone as a minor component therein. The ozone content of the gas stream and the flow rate of the gas stream are preferably selected such that the amount of ozone introduced to the blood aliquot, either on its own or in combination with other stressors, does not give rise to excessive levels of cell damage such that the therapy is rendered ineffective. Suitably, the gas stream has an ozone content of up to about 300 µg/ml, preferably up to about 100 µg/ml, more preferably about 30 µg/ml, even more preferably up to about 20 µg/ml, particularly preferably from about 10 µg/ml to about 20 µg/ml, and most preferably about 14.5±1.0 µg/ml. The gas stream is suitably supplied to the aliquot at a rate of up to about 2.0 liters/min, preferably up to about 0.5 liters/min, more preferably up to about 0.4 liters/min, even more preferably up to about 0.33 liters/min, and most preferably about 0.24±0.024 liters/min, at STP. The lower limit of the flow rate of the gas stream is preferably not lower than 0.01 liters/min. more preferably not lower than 0.1 liters/min, and even more preferably not lower than 0.2 liters/min.

The electromagnetic emission stressor is suitably applied by irradiating the aliquot under treatment from a source of an electromagnetic emission while the aliquot is maintained at the aforementioned temperature and while the oxygen/ozone gaseous mixture is being bubbled through the aliquot. Preferred electromagnetic emissions are selected from photonic radiation, more preferably UV, visible and infrared light, and even more preferably UV light. The most preferred UV sources are UV lamps emitting primarily UV-C band wavelengths, i.e. at wavelengths shorter than about 280 nm. Such lamps may also emit amounts of visible and infrared light. Ultraviolet light corresponding to standard UV-A (wavelengths from about 315 to about 400 nm) and UV-B (wavelengths from about 280 to about 315) sources can also be used. For example, an appropriate dosage of such UV light, applied simultaneously with the aforementioned temperature and oxidative environment stressors, can be obtained from up to eight lamps arranged to surround the sample container holding the aliquot, operated at an intensity to deliver a total UV light energy at the surface of the blood of from about 0.025 to about 10 joules/cm$^2$, preferably from about 0.1 to about 3.0 joules/cm$^2$, may advantageously be used. Preferably, four such lamps are used.

The time for which the aliquot is subjected to the stressors is normally within the time range of up to about 60 minutes. The time depends to some extent upon the chosen intensity of the electromagnetic emission, the temperature, the concentration of the oxidizing agent and the rate at which it is supplied to the aliquot. Some experimentation to establish optimum times may be necessary on the part of the operator, once the other stressor levels have been set Under most stressor conditions, preferred times will be in the approximate range of from about 2 to about 5 minutes, more preferably about 3 or about 3½ minutes. The starting blood temperature, and the rate at which it can be warmed or cooled to a predetermined temperature, tends to vary from subject to subject. Such a treatment provides a modified blood aliquot which is ready for injection into the subject.

In the practice of the preferred process of the present invention, the blood aliquot may be treated with the stressors using an apparatus of the type described in U.S. Pat. No. 4,968,483 to Mueller. The aliquot is placed in a suitable, sterile, UV light-transmissive container, which is fitted into the machine. The UV lamps are switched on for a fixed period before the gas flow is applied to the aliquot providing the oxidative stress, to allow the output of the UV lamps to stabilize. The UV lamps are typically on while the temperature of the aliquot is adjusted to the predetermined value, e.g. 42.5±1° C. Then the oxygen/ozone gas mixture, of known composition and controlled flow rate, is applied to the aliquot, for the predetermined duration of up to about 60 minutes, preferably 2 to 5 minutes and most preferably about 3 minutes as discussed above, so that the aliquot experiences all three stressors simultaneously. In this way, blood is appropriately modified according to the present invention to achieve the desired effects.

A subject preferably undergoes a course of treatments, each individual treatment comprising removal of a blood aliquot, treatment thereof as described above and re-administration of the treated aliquot to the subject. A course of such treatments may comprise daily administration of treated blood aliquots for a number of consecutive days, or may comprise a first course of daily treatments for a designated period of time, followed by an interval and then one or more additional courses of daily treatments.

In one preferred embodiment, the subject is given an initial course of treatments comprising the administration of 4 to 6 aliquots of treated blood. In another preferred embodiment, the subject is given an initial course of therapy comprising administration of from 2 to 4 aliquots of treated blood, with the administration of any pair of consecutive aliquots being either on consecutive days, or being separated by a rest period of from 1 to 21 days on which no aliquots are administered to the patient, the rest period separating one selected pair of consecutive aliquots being from about 3 to 15 days. In a more specific, preferred embodiment, the dosage regimen of the initial course of treatments comprises a total of three aliquots, with the first and second aliquots being administered on consecutive days and a rest period of 11 days being provided between the administration of the second and third aliquots. In the method of the invention, it is preferred that no more than one aliquot is administered to the subject on any given day.

It may be preferred to subsequently administer additional courses of treatments following the initial course of treatments. Preferably, subsequent courses of treatments are administered at least about three weeks after the end of the initial course of treatments. In one particularly preferred embodiment, the subject receives a second course of treatments comprising the administration of one aliquot of treated blood every 30 days following the end of the initial course of treatments, for a period of 6 months.

It will be appreciated that the spacing between successive courses of treatments should be such that the positive effects of the treatment of the invention are maintained, and may be determined on the basis of the observed response of individual subjects.

As discussed above, the method of the present invention may preferably be used as an adjunctive treatment in combination with other therapies for CHF. Preferred examples of such other therapies include one or more of ACE inhibitors, β-blockers, aldosterone antagonists, TNF blockers, suppressors of TNF production and other forms of routine therapy.

The invention is further illustrated and described with reference to the following specific examples.

EXAMPLE 1

This example describes a study conducted to determine the effect of the treatment of the invention on endothelial function in Watanabe rabbits. known to develop complex atherosclerotic lesions during the first year of life. As previously mentioned, endothelial dysfunction is linked to the pathophysiology of CHF.

The rabbits entered the study at 7 to 8 months of age, and were randomized into three groups, a first group to be sacrificed immediately for baseline measurements, a second group (n=10) which received injections of blood treated according to the invention, and a third group (n=10) which received sham treatments comprising injections of untreated blood.

The treatment comprised a total of 4 injections of treated blood over a period of 10 weeks. The blood was treated by exposure to the following three stressors in an apparatus as generally described in U.S. Pat. No. 4,968,483 to Mueller et al.:

(a) an elevated temperature of 42.5° C.±1.0° C.:

(b) a gas mixture of medical grade oxygen containing 14.5±1.0 μg/ml of ozone, bubbled through the blood at a flow rate of 240±24 ml/min for 3 minutes; and (c) ultraviolet light at a wavelength of 253.7 nm, and a total energy density of 2.0 joules/cm² with some fluctuation within the previously mentioned range).

The treated blood was administered to the animals by intra-muscular injection. The control animals were administered intramuscular injections of untreated blood on the same injection schedule as the treated animals.

All animals were sacrificed at 11 months of age. Ring preparations were taken from the iliac arteries of the animals and were evaluated for the amount of relaxation induced by acetylcholine (an endothelial-dependent vasodilator) after being treated with phenylephrine (a vasoconstrictor).

Evaluation of the ring preparations showed a significant increase in endothelial-mediated vasorelaxation (52.2±6%) was observed in the treated animals as compared to the control animals injected with untreated blood (22.9±4%, p less than 0.001 ).

No relaxation was observed when the endothelium was removed from the ring preparations, further confirming the endothelium-specific effect of the treatment of the invention.

EXAMPLE 2

This example describes a study into the effects of the treatment of the invention therapy on patients suffering from peripheral vascular disease (PVD). The study was conducted at the University Hospital, Lund, Sweden.

The study comprised a placebo-controlled, double blind study In 18 patients (7 males, 11 females) with moderately advanced PVD, whose main symptom was intermittent claudication. The patients participating in the study were recruited from the attending population of the Department of Internal Medicine of the University Hospital, Lund, Sweden.

The patients were randomly assigned to receive either placebo (intramuscular injection of 10 ml warm saline) or treatment according to the invention comprising intramuscular injections of 10 ml of treated autologous blood. The treatment of the blood Involved the collection of a 10 ml aliquot of a patient's venous blood into 2 ml of sodium citrate 3–4% as anticoagulant. Each blood aliquot was transferred to a sterile, disposable low-density polyethylene vessel and then exposed to the following conditions in an apparatus as generally described in U.S. Pat. No. 4,968,483 to Mueller et al.:

(d) elevated temperature of 42.5° C.;

(e) medical oxygen containing 14.5±1.0 μg/ml of ozone bubbled through the blood aliquot at a flow rate of 240±24 ml/min at STP for 3 minutes; and (f) ultra-violet light at a wavelength of 253.7 nm, and a total energy of about 2.0 joules/cm².

Each patient received a total of 12 injections of saline or treated blood over a period of 9 weeks.

The therapy was assessed by measuring the recovery rate of skin blood flow and oxygen tension following total temporary occlusion of blood flow in the extremities of each patient prior to commencement of the therapy and at 3 weeks, 6 weeks, 9 weeks and 2 months following the initiation of the therapy.

Skin blood flow in the foot was measured by Laser Doppler Fluxmetry (LOF) and oxygen tension was determined by measurement of transcutaneous skin oxygen pressure ($TcpO_2$) in the foot In patients receiving the treatment of the invention, a strong trend was observed toward a treatment-related reduction in both the total time to reach maximum perfusion ($TP_H$) and the halftime to reach maximum perfusion ($T_{1/2}P_H$), indicative of an improvement in the rate of recovery of skin blood flow. No change was observed in the control group.

The improved rate of recovery of blood flow in patients treated according to the invention was apparent during the course of treatments and persistent throughout, but did not reach significance until 2 months following initiation of the therapy. A comparison of the $T_{1/2}P_H$ for the placebo and treated groups, as measured by LDF, is shown in FIG. 1.

There was also an observed trend toward more rapid recovery of skin oxygen content in the treated group. This difference became statistically significant at 2 months following the initiation of the therapy. A comparison of the half-time to maximum $TcpO_2$ after ischemia ($O_2T_{1/2}$) for the treated group compared to the placebo group Is shown in FIG. 2.

The study therefore demonstrated that, in this group of moderately advanced PVD patients, the treatment of the invention had a dear biological effect on the rate at which blood flow in the skin of the foot was recovered following a period of total occlusion ischemia. A similar effect, but of smaller magnitude, was noted for the rate of $TcpO_2$ recovery, whereas patients receiving placebo treatment showed no change. These results suggest that the treatment of the invention has a beneficial effect on endothelial function, and appears to improve skin microcirculatory function in patients with PVD.

EXAMPLE 3

This example relates to the use of the treatment of the invention to prevent the onset of arthritis, and describes the results of a study conducted in an established animal model of arthritis. The specific animal model used in this study was adjuvant-induced arthritis in rats (see, for example. Pearson, C., 1956, "Development of Arthritis, periarthrtis and periostitis in rats given adjuvant", *Proc. Soc. Exp. Biol. Med.*, 91:95). According to this model, arthritis is induced in rats by injecting them with adjuvant containing *Mycobacterium butyricum*.

Male Lewis rats, 4 to 5 weeks of age, 100 to 120 g, were obtained from Charles River Laboratories, quarantined one week and entered into the study. An adjuvant mixture was prepared for induction of arthritis by suspending 50 mg *M. butyricum* (Difco Laboratories, Inc., Detroit, Mich.) in 5 ml light white paraffin oil-m3516 (Sigma Chemical Co., St. Louis, Mo.) and thoroughly mixed using a homogenizer. Aliquots of the mixture sufficient to supply 0.15 mg *M. butyricum* was injected Into each animal subcutaneously, at the base of the tail. Symptoms of arthritis appeared about 12 days after induction, in each animal, as evidenced by limb swelling.

Two rats, which were not injected with the adjuvant mixture, were used as blood donors. Blood was collected from the donors by cardiac puncture, and 10 ml of citrated blood was transferred to a sterile, low density polyethylene vessel for ex vivo treatment with stressors according to the invention. Using an apparatus as generally described in the above-mentioned Mueller patent, the blood was stressed by a treatment according to the invention.

Six animals were given a course of 2 injections of 0.2 ml aliquots of the treated blood, the injections being administered on consecutive days after the onset of arthritis. A control group of 8 rats received injections of untreated blood using the same injection schedule as the treated animals. Injections commenced one day after the induction of arthritis. Hind paw volumes of the animals were measured, on alternate days, after onset of arthritis, by water displacement in a 250 ml beaker using a top-loaded Mettler balance. The results for each group of animals were averaged and are presented graphically on the accompanying FIG. 3, a plot of mean foot volume against days after induction of arthritis.

The upper curve is derived from the control group of animals, the lower curve from the animals which received the course of injections of treated blood. A significant decrease in the severity of the arthritis, as indicated by lower foot volumes, is apparent for the treated animals as compared to the animals of the control group.

The above results show that treatment of subjects with modified mammalian blood can effectively prevent the onset of arthritis in mammals.

The expression of IL-6 mRNA in lymph nodes of treated and untreated animals was measured 10 days after induction of arthritis, and the

TABLE I

| Treatment | IL-6 copy no. (per 4500 actin units) |
|---|---|
| Active | <35 (n = 8) |
| Control | 254 ± 203 (n = 8) |

The results shown above in Table 1 show that the treatment according to the invention can modulate levels of inflammatory cytokines in a Th1/TNF-α-dependent model of arthritis. There is evidence that production of inflammatory cytokines such as IL-6 and TNF-α is linked to the pathophyslology of CHF.

EXAMPLE 4

The experiment reported in this example demonstrates, by use of an animal model system involving ischemia and subsequent reperfusion of various body organs, that the treatment of the present invention has the effect of reducing apoptosis and necrosis. Ischemia-reperfusion injuries are known to involve increase of apoptosis and necrosis in the affected organs and tissues-see for example Saikumar p, et al. "Mechanisms of cell death in hypoxial/reoxygenation injury", *Oncogene* 1998 Dec 24; 17(25):3341–9; and Burns A. T. et.al., "Apoptosis in ischemia/reperfusion injury of human renal allografts" *Transplantation* 1998 Oct 15; 66(7): 872–6, and other publications both preceding and following those. Known techniques of determination of apoptosis at the cellular level are employed in this example.

Pure-bred normal beagle dogs, aged 1–2 years, equal numbers of males and females, were used as the experimental animals. The animals were separated into four groups, A, B, C and D, each group consisting of six animals. three males and three females. Animals of groups A and C were subjected to the process of the invention, by being subjected to two 10-day courses of daily removal of an 8 ml aliquot of blood, extracorporeal treatment of the aliquot with oxygen/ ozone, UV radiation and heat, and re-administraion of 5 ml of the treated aliquot to the same animal, by intramuscular injection.

Each such treatment was conducted as follows.

An 8-lm aliquot of blood was extracted from the animal, treated with sodium citrate (2 ml) and placed in a sterile container. It was subjected simultaneously to the UV radiation, oxygen/ozone gas oxidative environment and elevated temperature stressors, in an apparatus as generally described in the aforementioned Mueller U.S. Pat. No. 4,969,483. More specifically, the blood sample in the sterile, UV-transparent container was heated using infra-red lamps to 42.5° C., and whilst being maintained at that temperature, it was subjected to UV radiation of predominant wavelength 253.7 nm under the preferred conditions previously described. Simultaneously, a mixture of medical grade oxygen and ozone, of ozone content 13.5–15.5 µg/ml was bubbled through the blood sample at a flow rate within the range from 60–240 mls/min (STP). The time of simultaneous UV exposure and gas mixture feed was 3 minutes. A 5 ml portion of the treated blood aliquot was reinjected intramuscularly into each test animal.

Each animal of groups A and C, receiving the courses of treatment according to the invention, experienced a three week rest period between the 10-day courses of treatment Groups B and D were the control groups, given two 10-day courses of daily injections of 5 ml of physiological saline, with a three-week rest period between the 10-day courses.

One day following the second course of injections, the animals were anaesthetized under light gas anaesthesia, and the right kidney of each animal was removed through a back incision. An occlusive clip was placed on the remaining renal artery and vein, to expose the left kidney to transient ischemia, for 60 minutes. Then the clip was removed to allow reperfusion of the kidney by normal blood flow.

The animals were observed for 6 days after the ischemia procedure, and then sacrificed. The ischemic kidney of each animal was surgically removed and divided into two parts. One part was kept frozen at −80° C., and the other part was fixed in 10% formalin for immuno- and routine histopathology studies.

Mitochondrial membrane potential was measured in proximal tubular cells isolated from the ischemic and control kidneys, both at the time of removal of the control kidney and following sacrifice. For this purpose, dog kidney proximal tubes were purified from normal or ischemic kidney cortexes by the collagenase treatment procedure described by Marshansky et al., "Isolation of heavy endosomes from dog proximal tubes in suspension", *J.Membr. Biol* 153(1), 59–73, 1996. Renal mitochondria were isolated in suspension by differential centrifugation (see Marshansky, "Organic hydroperoxides at high concentrations cause energization and activation of AATP synthesis in mitochondria", *J. Biol. Chem.* 264(7), 3670–3673, 1989. after tissue homogenization in a buffer containing 250 mM sucrose, 10 mM HEPES-Tris (pH 7.5), and 250 µM EDTA. Cell debris was removed by centrifugation at 10,000 g for 30 minutes. The mitochondria were washed with the sucrose/HEPES buffer without EDTA.

Mitochondrial membrane potential was measured as described by Kroemer, G., Zamzam, N. and Susin, S.A., "Mitochondrial control of apoptosis", (Review) *Immunology Today* (1997) v.18, p 44–51; with JC-1 dye-see Salvioli et.al., "JC-1, but not DiOC6(3) or rhodamine 123, is a reliable fluorescent probe to assess delta psi changes in intact cells: implications for studies on mitochondrial functionality during apoptosis", *FEBS Letters* 411 (1), 77–82. 1987. JC-1 fluorescence in the suspension of purified mitochondria from normal and ischemic kidneys was monitored continuously on a Deltascan Model RFM-2001 spectrofluorimeter (Photon Technology International, South Brunswick, N.J.). The excitation wavelength was 490 nm (slit width 2 nm) and the emission wavelength was 590 nm (slit width 4 nm). The signals were recorded using Felix® (Version 1.1) software. All measurements were performed with continuous stirring at 37° C. The incubation buffer for measurement of mitochondrial membrane potential contained 200 mM sucrose, 5 mM $MgCl_2$, 5 mM $KH_2PO_4$, 0.1 µM of JC-1 and 30 Mm HEPES-Tris (pH 7.5). The concentrations of the substrate and inhibitors were 10 mM succinate, 0.1 µM rotenone with or without 0.1 µM FCCP. Proximal tubule mitochondrial membrane potential was estimated in the right (control) kidney prior to ischemia and in the left (ischemic) kidney after sacrifice of the dogs on day 6 following ischemia and was estimated as difference of JC-1 fluorescence after uncoupling of mitochondria with FCCP as shown in the accompanying FIG. 4A. For each measurement, 50 µg protein of purified material was used.

JC-1 fluorescence is proportional to the mitochondrial membrane potential. The contralateral nephrectomized kidney served as control. As is clear from the FIG. 4B, the treatment process of the invention did not modify the membrane potential of the non-ischemic control right kidney (p=445 for treated vs saline). However, the ischemic kidney of the saline-injected animals showed significantly lower ($p<0.05$) fluorescence compared to the control kidney. The stress treatment according to the invention prevented the uncoupling of mitochondria during ischemic/reperfusion, and membrane potential showed no significant difference (p=0.244) between ischemic and control kidneys. This parameter remained significantly higher (p=0.0006) vs saline-injected dogs) in the ischemic kidneys of dogs pretreated according to the process of the invention for at least 6 days post-reperfusion.

These results indicate that the process of the invention effects protection of the kidney against apoptosis and/or accelerates recovery at the mitochondrial level. Accordingly the process of the invention is indicated for reconditioning of the cells, tissues and organs of a mammalian body against subsequently encountered factors which will normally accelerate apoptosis.

Specifically, the preservation of mitochondrial membrane potential evidences the capacity of the therapy to protect mitochondria, and thereby to precondition cells against apoptosis.

EXAMPLE 5

A group of 12 male SHR rats was treated with either injections of pooled blood stressed as described in Example 4 above, or, in control animals, with injections of saline. Since the blood from all of the animals of this genetic strain is identical, blood from one animal of this same strain was treated by the process of the invention for administration to the test animal. The blood was treated with sodium citrate as anti-coagulant, and placed in a sterile container They received either injections of 150 µl of stressed blood on days −14 and −13 followed by a rest period of 11 days and a third injection the day before ischemic surgery, or injections in parallel with saline. On the day of surgery, the rats were anaesthetized with light flurane, and the right kidney was removed through a mid-abdominal incision. The left kidney was then subjected to transient ischemia by occlusion of the left renal artery and vein using a micro-clip. The skin was then temporarily closed. After 60 minutes of occlusion, the clip was removed and the wound was closed with a suture. The animals were sacrificed 12 hours after reperfusion.

The ischemic and non-ischemic kidneys of the test animals were removed and subjected to DNA laddering tests. Oligonucleosomal DNA fragmentation into 180 to 200 base pairs is a specific pattern which appears as a ladder after agarose gel electrophoresis in various organs undergoing apoptosis. To estimate the degree of DNA fragmentation in the kidney cortex, an aliquot of pulverized kidney cortex was weighed and total tissue DNA was extracted by the phenol chloroform procedure after tissue digestion with proteinase K and RnaseA in the presence of EDTA. One µg of extracted DNA was labeled by enyrnatic assay using terminal deoxynudeotidyl transforase with $P^{32}$-dCTP (see Teiger et.al., 'Apoptosis in pressure overload-induced heart hypertrophy in the rat,' *J. Clin. Invest* 97,2891–2897, 1996). Increasing quantities of radio-labelled DNA were loaded onto 1.5% agarose gels. After electrophoresis. DNA was transferred onto nylon membranes (Hybond) and the radioactivity associated with 150 to 1500 bp DNA fragments was quantified in a Phosphorlmager (Molecular Dynamics). A regression line for each sample was drawn for the radioactivity as a function of DNA loaded on the gel (see deBlois et.al., 'Smooth muscle cell apoptosis during vascular regression in spontaneously hypertensive rats.' *Hypertension* 29, 340–349, 1997). The slope of the linear regression line served as a DNA fragmentation index (cpm/pixel per µg DNA).

The results from ischemic-reperfused (I/R) kidneys and from normal, non-IR kidneys, all from animals which did not receive injections of stressed blood, are shown graphically on FIG. 5, a plot of the slope of the regression lines for the various samples (vertical axis) against time after initiation of reperfusion. The DNA laddering, indicative of DNA fragmentation, was dearly increased in the ischemic kidney cortex compared to the contralateral non-ischemic organ and the maximal attained at twelve hours returned to near basal values by 48 hours. Twelve hours was thus selected as the tine point for study of the effect of the stressed blood of the invention on early ischemia-induced renal apoptosis.

FIG. 6A of the accompanying drawings is a picture of the electophoresis gel of the fragmented DNA, in the 150–1500 bp range, radio-labeled as described to attach radioactivity labels to the DNA fragments. Trace S derives from DNA of kidneys from animals which received saline injections prior to kidney ischemia-reperfusion, and trace V derives from DNA of kidneys of animals which received injections of the stressed blood prior to kidney ischemia-reperfusion. The Figure shows that 60 minutes renal ischemia induced a dear accumulation of fragmented DNA in both groups of rats at 12 h but the level of this parameter was significantly lower ($p<0.05$) in animals receiving the treated blood. FIG. 6B quantifies the amount of irradiation from the samples, in arbitrary units, and shows that DNA fragmentation-laddering occurs in both S and V samples as a result of ischemia/reperfusion, but that the extent is markedly reduced in V samples as compared with S samples. The results presented on FIG. 6B are the means of six animals in each case.

These results confirm that the cytoprotective effect of the administration of stressed blood according to the invention on renal reperfusion injury involves the inhibition of early or late apoptosis.

The ability of the treatment of the invention in reducing apoptosis in the kidney following ischemia/reperfusion during the early phase of apoptosis (after 12 hours) as determined by DNA laddering and density of apoptotic nuclei stained by Tdt is shown in FIGS. 7 and 8, respectively. As well, FIG. 3B shows that cell numbers in the kidney following ichemia/reperfusion were also significantly higher in the animals treated according to the invention.

EXAMPLE 6

This example describes the treatment of a small number of human patients with advanced chronic congestive heart failure. The patients had NYHA class III–IV chronic congestive heart failure with a left ventricular ejection fraction (LVEF) of less than 40% and a 6 minute walk distance of less than 300 m. Some of the patients had previously received other CHF treatments.

Protocol:

Patients receive a number of injections of treated blood. The 30 treatment schedule comprises injections on days 1, 2 and 14, followed by a single injection every 30 days for 5 months, each injection having a volume of 10 ml. Each individual treatment comprises the following steps: 1. Collection of 10 ml of a patient's own venous blood into 2 ml of 3–4% sodium citrate for injection, USP. The sodium cirate is added to the sample to prevent the blood from coagulating during the treatment 2. Transfer of the citrated blood sample to a sterile, disposable, low-density polyethylene vessel. 3. Ex vivo treatment of the blood sample by simultaneous exposure to;

an elevated temperature of $42.5 \pm 1.0°$ C.

a gas mixture of medical grade oxygen containing $14.5 \pm 1.0$ µg/ml of ozone which is bubbled through the blood sample at a flow rate of $240 \pm 24$ ml/min (at STP); and ultraviolet light at a wavelength of 253.7 nm. 4. Transfer of the blood sample from the sterile disposable container to a sterile syringe. 5. Intramuscular injection of 2 ml or 10 ml of the treated blood sample into the gluteal muscle of the same patient, following a local anaesthetic (1 mL of 2% Novocain or equivalent) at the injection site.

The ex vivo treatment of the blood sample described in step (3) above is performed with an apparatus as generally described In U.S. Pat. No. 4,968,483 to Mueller et al. The blood sample is simultaneously exposed to all three stressors for a period of 3 minutes.

Assessment of CHF:

Patients are monitored for adverse events during each visit. As well, a post-treatment follow-up is conducted to monitor survival, hospitalizations, and significant adverse events.

The primary endpoints used to assess the effectiveness of the treatment are changes in 6-minute walking distance and/or NYHA functional classification. Secondary endpoints include: improvement in cardiac function, reduction in diuretic requirement reduction in hospitalization stay; and improvement in symptoms.

As demonstrated by the data described above, the treatment of the present invention has been shown to have significant biological activity in humans and in a number of animal model systems, all of which involve Th1/TNF-α dependent inflammatory responses. As mentioned above, it is believed that the treatment down-regulates the pro-inflammatory Th1-type immune response, for example by Increasing anti-inflammatory TH2 type cytokines, including IL-10. This would at least partially explain the ability of the treatment of the invention to produce therapeutic benefits in each of the three areas which characterize CHF.

Furthermore, there is evidence to suggest that the treatment of the invention is IL-10 dependent (FIG. 9 and Shahid S. et al., *Journal of Investigative Dermatology* 14, No.4, 2000), briging about an up-regulation of ant-inflammatory cytokines such as IL-10, and a down-regulation of TH-1 driven immune responses. It has also been proposed that IL-10 may be an important component of the cytokine network in CHF, as there appears to be a reduction in the level of IL-10 in relation to TNF-α in CHF (Yamaoka et al., *Jpn Circ J* 63: 951–956).

Although the invention has been described with reference to specific preferred embodiments, it will be appreciated that many variations may be made to the invention without departing from the spirit or scope thereof. All such modifications are intended to be included within the scope of the following claims.

What is claimed is:

1. A method of treating congestive heart failure (CHF) in a human patient suffering therefrom, comprising:
   (a) treating an aliquot of the patient's blood ex vivo with a stressor comprising a liquid oxidizing agent; and
   (b) administering the aliquot of blood treated in step (a) to the patient, wherein the aliquot has a volume sufficient to treat CHF in the patient.

2. The method of claim 1, wherein said stressor further comprises electromagnetic emissions and/or a temperature above or below body temperature.

3. The method of claim 1, wherein the liquid oxidizing agent is introduced into the blood aliquot in an amount which does not give rise to excessive levels of cell damage.

4. The method of claim 2, wherein the electromagnetic emission comprises ultraviolet light having one or more UV-C band wavelengths.

5. The method of claim 2, wherein the temperature to which the aliquot is cooled or heated is a temperature which does not result in substantial hemolysis of the blood in the aliquot.

6. The method of claim 5, wherein the mean temperature of the blood in the aliquot is in the range of from about 0° C. to about 36.5° C.

7. The method of claim 5, wherein the mean temperature of the blood in the aliquot is in the range of from about 10° C. to about 30° C.

8. The method of claim 5, wherein the temperature is in the range of from about 40° C. to about 50° C.

9. The method of claim 8, wherein the temperature is 42.5±1° C.

10. The method of claim 1, wherein the volume of the aliquot is up to about 400 ml.

11. The method of claim 10, wherein the volume of the aliquot is about 10 ml.

12. The method of claim 10, wherein the volume of the aliquot is about 2 ml.

13. The method of claim 1, wherein the aliquot is subjected to the stressor for a period of up to about 60 minutes.

14. The method of claim 13, wherein the aliquot is subjected to the stressor for a period of about 3 minutes.

15. The method of claim 1, wherein the blood is administered to the mammal by a method suitable for vaccination selected from the group consisting of intra-arterial injection, intramuscular injection, intravenous injection, subcutaneous injection, intraperitoneal injection, and oral, nasal or rectal administration.

16. The method of claim 2, wherein all of the stressors are simultaneously administered to the aliquot.

17. The method of claim 2, wherein any two of the stressors are simultaneously administered to the aliquot.

18. A combination treatment for congestive heart failure (CHF) in a human patient suffering therefrom, the combination treatment including the administration to the patient of an aliquot of the patient's own blood which has been treated ex vivo with a stressor comprising a liquid oxidizing agent and the administration of an agent selected from the group consisting of nitrates, β-blockers, ACE inhibitors, AT receptor blocking agents, aldosterone antagonists, calcium channel blocking agents, suppressors of production of TNF-α, sodium and fluid restriction, diuretics and digitalis wherein the aliquot has a volume sufficient to treat CHF in the patient.

19. The combination treatment of claim 18, wherein the suppressors of production of TNF-α are selected from the group consisting of pentoxifyline, TACE inhibitors, amrinone, adenosine, thalidomide and dexamethasone.

20. A method of treating congestive heart failure (CHF) in a human patient suffering therefrom, comprising:
   (a) treating an aliquot of the patient's blood ex vivo simultaneously, for a time from about 2–5 minutes, with a combination of stressors comprising (1) a liquid oxidizing agent; (2) ultraviolet light having one or more UV/C band wavelengths; and (3) temperature in the range of from about 37° C. to about 55° C.; and
   (b) administering the aliquot of the blood treated in step a) to the patient, wherein the aliquot has a volume sufficient to treat the CHF in the patient.

* * * * *

UNITED STATES PATENT AND TRADEMARK OFFICE
CERTIFICATE OF CORRECTION

PATENT NO. : 7,153,649 B2  
APPLICATION NO. : 10/278920  
DATED : December 26, 2006  
INVENTOR(S) : Eldon R. Smith and Guilermo Torre-Amione It is certified that error appears in the above-identified patent and that said Letters Patent is hereby corrected as shown below:

Title page, item (57):

In the Abstract, line 2, please replace "patents" with --patients--

Column 2, line 18, please replace "dassification" with --classification--

Column 3, line 26, please replace "occasion" with --occlusion--

Column 3, line 53, please replace "In" with --in--

Column 3, line 59, please replace "In" with --in--

Column 3, line 63, please replace "TNF-$\beta$" with --TNF-$\alpha$--

Column 3, line 66, please replace "TNF-$\beta$" with --TNF-$\alpha$--

Column 4, line 55, please replace "Plasma." with --plasma,--

Column 4, line 61, please replace "tion." with --tion,--

Column 5, line 1, please replace "In" with --in--

Column 5, line 5, please replace "subject" with --subject.--

Column 5, line 29, please replace "au" with --all--

Column 6, line 33, please replace "set" with --set.--

Column 7, line 44, please replace "rabbits." with --rabbits,--

Column 7, line 61, please replace "C.:" with --C.;--

Column 8, line 25, please replace "in" with --In--

Column 8, line 35, please replace "Involved" with --involved--

UNITED STATES PATENT AND TRADEMARK OFFICE
CERTIFICATE OF CORRECTION

PATENT NO. : 7,153,649 B2
APPLICATION NO. : 10/278920
DATED : December 26, 2006
INVENTOR(S) : Eldon R. Smith and Guilermo Torre-Amione It is certified that error appears in the above-identified patent and that said Letters Patent is hereby corrected as shown below:

Column 8, line 42, please replace "42.5° C.;" with --42.5° C.$\pm$1.0° C;--

Column 8, line 57, please replace "(LOF)" with --(LDF)--

Column 8, line 59, please replace "In" with --in--

Column 9, line 10, please replace "Is" with --is--

Column 9, line 44, please replace "Into" with --into--

Column 10, line 13, please replace ", and the" with --, and the results are presented below in Table 1.--

Column 11, line 39, please replace "1989." with --1989,--

Column 12, line 12, please replace "p = 445" with --p = 0.445--

Column 12, line 27, please replace "reconditioning" with --pre-conditioning--

Column 13, line 4, please replace "electrophoresis." with --electrophoresis,--

Column 13, line 16, please replace "non-IR" with --non-I/R--

Column 13, line 21, please replace "dearly" with --clearly--

Column 13, line 25, please replace "tine" with --time--

Column 13, line 35, please replace "dear" with --clear--

Column 14, line 3, please replace "The 30 treatment" with --The treatment--

Column 14, line 10, please replace "treatment 2." with --treatment. 2.--

UNITED STATES PATENT AND TRADEMARK OFFICE
CERTIFICATE OF CORRECTION

PATENT NO. : 7,153,649 B2
APPLICATION NO. : 10/278920
DATED : December 26, 2006
INVENTOR(S) : Eldon R. Smith and Guilermo Torre-Amione It is certified that error appears in the above-identified patent and that said Letters Patent is hereby corrected as shown below:

Column 14, line 23, please replace "mL" with --ml--

Column 14, line 27, please replace "In" with --in--

Column 14, line 39, please replace "requirement reduction" with --requirement;--

Column 14, line 48, please replace "Increasing" with --increasing--

Column 14, line 55, please replace "briging" with --bringing--

Column 14, line 55, please replace "ant" with --anti--

Signed and Sealed this

Sixth Day of May, 2008

JON W. DUDAS
*Director of the United States Patent and Trademark Office*